US008164742B1

(12) United States Patent
Carrieri et al.

(10) Patent No.: US 8,164,742 B1
(45) Date of Patent: Apr. 24, 2012

(54) PHOTOPOLARIMETRIC LIDAR DUAL-BEAM SWITCHING DEVICE AND MUELLER MATRIX STANDOFF DETECTION SYSTEM AND METHOD

(75) Inventors: Arthur H. Carrieri, Abingdon, MD (US); Erik S. Roese, Baltimore, MD (US); David J. Owens, Kingsville, MD (US); Jonathan C. Schultz, Perryville, MD (US); Michael V. Talbard, BelAir, MD (US); Pascal I. Lim, Baltimore, MD (US); Kevin C. Hung, Baltimore, MD (US); Jerold R. Bottiger, Aberdeen, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 1314 days.

(21) Appl. No.: 11/779,457

(22) Filed: Jul. 18, 2007

(51) Int. Cl.
*G01C 3/08* (2006.01)

(52) U.S. Cl. ...... 356/5.01; 356/3.01; 356/3.1; 356/4.01; 356/4.1; 356/5.1

(58) Field of Classification Search ......... 356/3.01–28.5
See application file for complete search history.

(56) References Cited

U.S. PATENT DOCUMENTS 6,060,710 A * 5/2000 Carrieri et al. ............. 250/338.1
6,389,408 B1 5/2002 Carrieri et al.

OTHER PUBLICATIONS

Carrieri A., et al "Photopolarimetric lidar dual-beam switching device and Mueller matrix standoff detection system and method" Journal of Applied Remote Sensing, vol. 1, 013502 (Jan. 19, 2007).

* cited by examiner

*Primary Examiner* — Luke Ratcliffe
(74) *Attorney, Agent, or Firm* — Ulysses John Biffoni

(57) ABSTRACT

An optomechanical switching device, a control system, and a graphical user interface for a photopolarimetric lidar standoff detection that employs differential-absorption Mueller matrix spectroscopy. An output train of alternate continuous-wave $CO_2$ laser beams [ . . . L1:L2 . . . ] is directed onto a suspect chemical-biological (CB) aerosol plume or the land mass it contaminates (S) vis-à-vis the OSD, with L1 [L2] tuned on [detuned off] a resonant molecular absorption moiety of CB analyte. Both incident beams and their backscattered radiances from S are polarization-modulated synchronously so as to produce gated temporal voltage waveforms (scattergrams) recorded on a focus at the receiver end of a sensor (lidar) system. All 16 elements of the Mueller matrix ($M_{ij}$) of S are measured via digital or analog filtration of constituent frequency components in these running scattergram data streams (phase-sensitive detection). A collective set of normalized elements $\{\underline{\Delta M_{i,j}}\}$ (ratio to $M_{11}$) susceptible to analyte, probed on-then-off its molecular absorption band, form a unique detection domain that is scrutinized; i.e., any mapping onto this domain by incoming lidar data—by means of a trained neural network pattern recognition system for instance—cues a standoff detection event.

17 Claims, 7 Drawing Sheets

| COMPOUND | |
|---|---|
| Ⓡ D-MANNOSE | [1,2] [2,3] |
| Ⓑ L-TARTARIC ACID | [1,3] [2,1] [3,1] [3,4] [4,3] |
| Ⓖ DL-TARTARIC ACID | [2,4] [4,2] |

PHOTOPOLARIMETRIC LIDAR DUAL-BEAM SWITCHING DEVICE AND MUELLER MATRIX STANDOFF DETECTION SYSTEM AND METHOD

GOVERNMENT INTEREST

The invention described herein may be manufactured, licensed, and used by or for the U.S. Government.

TECHNICAL FIELD

The present invention relates, in general, to a system and method for detecting chemical and biological materials at a distance. More particularly, the present invention relates to an optical switching device for use in a system for detecting and identifying target contaminants such as chemical or biological warfare materials (CBs), or simulants of such compounds at a distance, based on Mueller matrix spectroscopy.

BACKGROUND

Distant detection of chemical and/or biological warfare materials and contaminates (CBs) is vitally important to joint force and homeland security operations. Once the presence of a CB is detected at a location, preventive measures may be taken prior to entering the area. Intensive research is being conducted to develop systems that are able to perform rapid and reliable detection and identification of CBs at safe standoff distances.

In general, CB standoff detectors receive electromagnetic energy radiated from a target and attempt to identify substances present at the target from characteristics of the radiated energy. Some systems are passive and rely solely on detection of target luminescence and/or absorption/emission spectra in the presence of ambient electromagnetic energy. Other systems actively probe a target with electromagnetic beams and analyze scattering radiant spectra to identify the substances present. While CB detection systems using electromagnetic energy ranging from terahertz and long-wave infrared bands to ultraviolet have been tried, middle infrared (MIR) light has been found to be particularly useful since spectral bands lying in the MIR region can be found in which there are distinctive absorption spectra for CB molecular structures (the so-called MIR "fingerprint") and in which the natural atmosphere is essentially transparent. A variety of MIR CB sensing systems use scattered light to determine properties of CBs at a distance. While some systems measure only the intensity of backscattered light, others also attempt to collect and analyze polarization states to better characterize CB molecular structures.

One technique to obtain polarization data from backscattered light is differential absorption Mueller matrix spectroscopy (DIAMMS). A DIAMMS-based CB detection system is described in U.S. Pat. No. 6,060,710, issued on May 9, 2000 to Carrieri, et al. ("the '710 patent"), incorporated herein by reference as if fully set forth. In general, a DIAMMS system undertakes identification of unknown substances at a distance by probing a target surface or an aerosol cloud with at least two polarization-modulated middle infrared laser (MIR) beams. One beam (the "excitation" beam) is tuned to a known absorption/extinction wavelength for substances of interest to drive it into molecular vibrational resonance, and a second "reference" beam is tuned to a nearby offset wavelength at which there is essentially no absorption by substances of interest and thus nil resonant molecular vibrations. A detector collects the backscattered polarization modulated radiation or "scattergrams" for both beams. The scattergrams are time varying waveforms which can be Fourier transformed to extract complex frequency components from which excitation and reference Mueller matrices can be derived. A differential Mueller matrix may then be calculated from the excitation and reference matrices and mathematically analyzed to compare it with differential Mueller matrix models of known substances.

Improvements in CB identification by differential-absorption Mueller matrix spectroscopy have been desired. In particular, there is a need for a robust, reliable, field-ready selective CB standoff identification system.

SUMMARY

In accordance with one aspect, an Optical Switching Device (OSD) is employed to perform photopolarimeter beam switching functions in one or more embodiments of DIAMMS detection systems according to the present invention. In accordance with another aspect, a photopolarimetric lidar standoff detection system provides a plurality of laser beams, a plurality of spectrum analyzers and an OSD. The OSD provides means for configuring the system into a first mode of operation in which a first laser beam is directed to a first spectrum analyzer and a second laser beam is directed to a beam terminator; a means for configuring the system into a second mode of operation in which the first laser beam is directed to a beam terminator and the second laser beam is directed to a second spectrum analyzer; means for configuring the system into a third mode of operation in which the second laser beam is directed to a beam terminator and the first laser beam is directed to a backscatter surface; a means for configuring the system into a fourth mode of operation in which the first laser beam is directed to a beam terminator and the second laser beam is directed to a backscatter surface; and a means for configuring the system into a fifth mode of operation in which each of the laser beams are directed to a beam terminator.

In accordance with another aspect, a computer program includes instructions for operating a photopolarimetric lidar standoff detection system having an optical switching device, a plurality of laser beams and a plurality of spectrum analyzers. The program instructions include instructions to configure the optical switching device for a first mode of operation in which a first laser beam is directed to a first spectrum analyzer and a second laser beam is directed to a beam terminator. The program instructions also include instructions to configure the optical switching device for a second mode of operation in which the first laser beam is directed to a beam terminator and the second laser beam is to a second spectrum analyzer. The program instructions also include instructions to configure the optical switching device for a third mode of operation in which the second laser beam is directed to a beam terminator and the first laser beam is directed to a backscatter surface. The program instructions also include instructions to configure the optical switching device for a fourth mode of operation in which the first laser beam is directed to a beam terminator and the second laser beam is directed to a backscatter surface. The program instructions also include instructions to configure the optical switching device for a fifth mode of operation in which each of the laser beams are directed to a beam terminator.

In yet another aspect according to an embodiment of the present invention, the program instructions include instructions to provide a graphical user interface (GUI). The GUI may include icons representing one or more components of the multiple beam photopolarimetric lidar standoff detection system. The GUI also may include objects to receive control inputs from an operator. The GUI also may include a display of status information for the one or more components of the multiple beam photopolarimetric lidar standoff detection system as well as a display of measurement data provided by the photopolarimetric lidar standoff detection system.

DETAILED DESCRIPTION

Figure 1A:
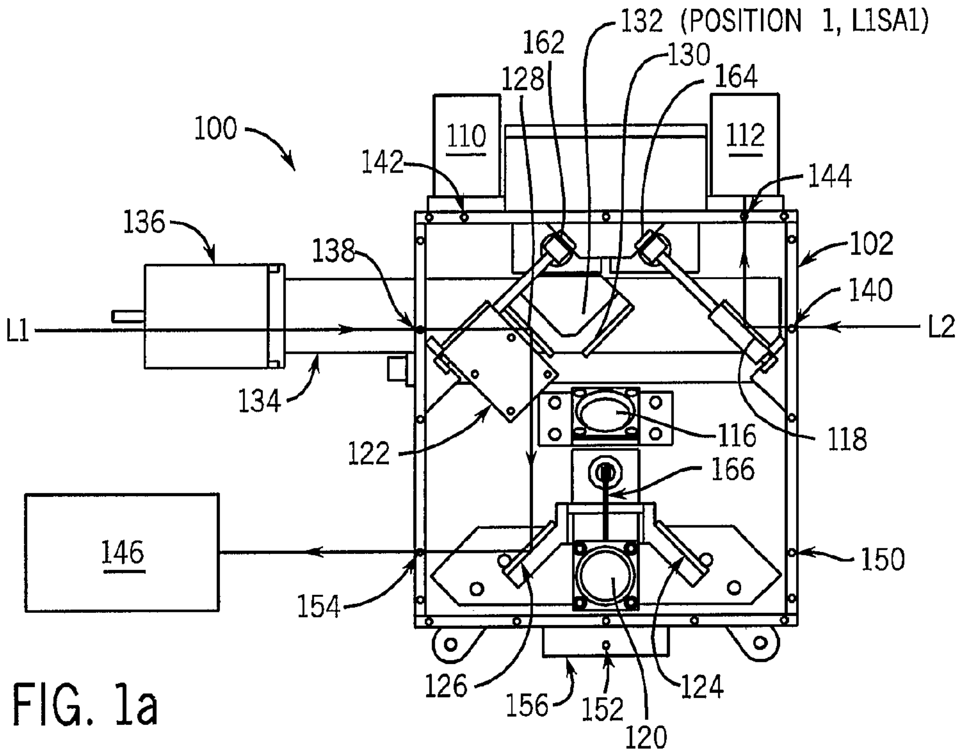
FIG. 1*a* is a top schematic view (with top plate removed) of the preferred embodiment of an Optical Switching Device according to the present invention in a first position/configuration.

The polarization state of a light beam can be completely represented by a 1×4 vector known as the Stokes vector. When a light beam is scattered by a body or changed by an optical element, the Stokes vector s of the light beam undergoes a linear transformation to a new Stokes vector s'. This transformation can be represented by a 4×4 matrix called the Mueller matrix (M), i.e., s'=Ms. By definition, s and s' are parameterized in real terms of complex amplitude and phase of the beam's electric field (E-field) orthogonal components. Accordingly, since the Stokes vector contains all the polarization information for a beam of light, the Mueller matrix contains all the polarization information in an elastic scattering process. Moreover, M may be used to derive physical and geometrical properties to uniquely characterize S, where S has a complex refractive index N=η(λ)+iξ(λ) and polar-azimuth angle orientation dependencies θ and φ, respectively, relative to the normal vector n of infinitesimal surface element dS and incident electromagnetic wave vector k.

A Jones (complex matrix J)-Pauli (real matrices $\sigma_i$, $\sigma_j$) representation of the Mueller matrix (real M) may be expressed in this form:

$$M = \frac{1}{2}\begin{pmatrix} |J_{\square\square}|^2 + |J_{\square\perp}|^2 + |J_{\perp\square}|^2 + |J_{\perp\perp}|^2 & |J_{\square\square}|^2 - |J_{\square\perp}|^2 + |J_{\perp\square}|^2 - |J_{\perp\perp}|^2 & 2\mathrm{Re}(J_{\square\square}J^*_{\square\perp} + J_{\perp\perp}J^*_{\perp\square}) & 2\mathrm{Im}(J_{\square\square}J^*_{\square\perp} - J_{\perp\perp}J^*_{\perp\square}) \\ |J_{\square\square}|^2 + |J_{\square\perp}|^2 - |J_{\perp\square}|^2 - |J_{\perp\perp}|^2 & |J_{\square\square}|^2 - |J_{\square\perp}|^2 - |J_{\perp\square}|^2 + |J_{\perp\perp}|^2 & 2\mathrm{Re}(J_{\square\square}J^*_{\square\perp} - J_{\perp\perp}J^*_{\perp\square}) & 2\mathrm{Im}(J_{\square\square}J^*_{\square\perp} + J_{\perp\perp}J^*_{\perp\square}) \\ 2\mathrm{Re}(J_{\square\square}J^*_{\perp\square} + J_{\perp\perp}J^*_{\square\perp}) & 2\mathrm{Re}(J_{\square\square}J^*_{\perp\square} - J_{\perp\perp}J^*_{\square\perp}) & 2\mathrm{Re}(J_{\square\square}J^*_{\perp\perp} + J_{\square\perp}J^*_{\perp\square}) & 2\mathrm{Im}(J_{\square\square}J^*_{\perp\perp} + J_{\square\perp}J^*_{\perp\perp}) \\ -2\mathrm{Im}(J_{\square\square}J^*_{\perp\square} - J_{\perp\perp}J^*_{\square\perp}) & -2\mathrm{Im}(J_{\square\square}J^*_{\square\perp} + J_{\perp\perp}J^*_{\square\perp}) & -2\mathrm{Im}(J_{\square\square}J^*_{\perp\perp} + J_{\square\perp}J^*_{\perp\square}) & 2\mathrm{Re}(J_{\square\square}J^*_{\perp\perp} - J_{\square\perp}J^*_{\perp\square}) \end{pmatrix},$$

where the elements are derived from $M_{ij}=\frac{1}{2}\,\mathrm{tr}\,\sigma_i J \sigma_j J^\dagger$. Inverting $M_{ij}$ to extract physical (N) and structural (particle shape and size) properties of scatterer S are active areas of research.

In connection with the present invention, a distant scatterer surface S may comprise a disseminated threat-agent CB aerosol plume or a CB substance deposited on land. A typical scenario may include: (i) an ambient aerosol plume as generated from a detonated projectile or as released from an aircraft; and (ii) the aftermath surface contamination coverage when contaminated rain deposits and settles onto/within terrain (e.g., soil, sand) or synthetic inhomogeneous dielectrics (e.g., asphalt, concrete).

In general, in the preferred embodiment according to the present invention, two polarization-modulated continuous-wave laser beams are tuned to nearby middle-infrared wavelengths in the region of absorption bands of the molecules of interest (i.e., 9.1-12.1 μm). These two beams are alternately transmitted in the form of a symmetric square wave-train $[\ldots \mathbf{L1}{:}\mathbf{L2} \ldots]_{transmit}$ to a suspected surface contaminant or airborne aerosol analyte (S). L1 and L2 are preferably emitted by regular and isotopic $CO_2$ laser waveguide cavities. Switching between beams is accomplished through a feedback controlled optomechanical switching device 100. The sent beams interrogate and target constituent CB molecules of surface/mass S in the following manner: absorption of E-field by beam L1, referred to as the 'analytic' probe laser beam, drives a bonded "backbone" primary group of threat agent molecules into a fundamental rock, stretch, or wag resonance vibration mode while the E-field of alternate beam L2, referred to as the "reference" probe laser beam, is totally scattered since it is detuned completely off all absorption cross-sections of molecular target 5, thus relaxing the molecular vibration resonance state. Furthermore, the E-fields of beams L1 and L2 are each polarization-modulated at separate frequencies in the range of 30-100 KHz, in order to obtain two Mueller matrix responses from which a differential-absorption Mueller matrix response (ΔM) from excited CB molecules is derived (L1: vibration resonance mode, part laser beam scattering, part absorption, relative to L2: off resonance relaxation mode, all laser beam scattering). Polarization-modulation actions on alternate incident and backscattering beams (which are performed independently on $[\ldots \mathbf{L1}{:}\mathbf{L2} \ldots]_{transmit}$ and $[\ldots \mathbf{L1}{:}\mathbf{L2} \ldots]_{receive}$) make possible the electronic measurement of a unique discriminate of the analyte; i.e., a susceptible group of differential-absorption Mueller matrix elements ΔM.

The term "polarization-modulation" is used in this disclosure in an optical encoding context. It entails the use of optical stress-birefringence elements to modulate the probe-interrogation laser beams sent to surface S as well as the backscattered beams received from surface S. This is accomplished in the preferred embodiment by means of two photoelastic modulation (PEM) operations induced on [ . . . L1:L2 . . . $]_{transmit}$ and [ . . . L1:L2 . . . $]_{receive}$ beams via stress-birefringent crystals. The PEM modulators preferably employ infrared-transparent salt ZnSe crystals with anti-reflection coatings on the front and back planer surfaces (and other IR materials including a single-crystal Ge that is cleaved, polished, and coated, as would be known to those of skill in the art). An oscillatory birefringence is induced at opposite ends of the cleaved crystal across its symmetry plane. In the preferred embodiment, a bonded piezoelectric transducer element (T) drives the ZnSe slab, at opposite ends, into its natural mechanical resonant frequency. With the crystal in harmonic mechanical resonance, the components of the E-fields of laser beams L1 and L2 that are aligned along the slow or extraordinary axis (eo-axis) and center of crystal aperture experience a periodic phase delay in transmission expressed as: $\delta=\delta_0 \cos \omega t$, where $\delta_0$ is the maximum amplitude of phase retardation in the beam's traversing electromagnetic wave (and the maximum compression of crystal), cos ωt is the oscillatory phase delay, and ω is frequency of the transducer element driving the crystal's compression-relaxation action-reaction. There is essentially no delay in the orthogonal components of the E-fields of beams traversing the fast or ordinary axis of ZnSe crystal (o-axis, which is perpendicular to eo-axis of crystalline structure), i.e., δ=0. This non-linear property of the crystal, δ, is called stress-birefringence. Accordingly, orthogonal components of the E-field of an incident beam linearly polarized at 45° to the PEM (i.e., exactly between eo- and o-axes of the crystal) add vectorally at the ZnSe-air exit plane producing polarization states that sweep in a continuum from left-to-right through linear, elliptical, and circular states at the frequency $\omega_1$ [viz, photoelastic modulation (PEM) action]. Thus, surface target S experiences probe beams [ . . . L1:L2 . . . $]_{transmit}$ with this periodic polarization continuum property. The backscattering response or echo in [ . . . L1:L2 . . . $]_{receive}$ is, furthermore, polarization-modulated a second time at a distinct frequency $\omega_2$ by a separate PEM centered on-axis in a receiver end that includes optical elements with a detector/sensor at the focus.

This combination of polarization modulations on incident beams and their backscattered radiances provides an electromagnetic encoding that makes possible a simultaneous measurement of M-elements of S, as described below.

Embodiments of DIAMMS-based photopolarimetric lidar (LIght Detection And Ranging (LIDAR)) systems according to the present invention preferably include a linear polarizer (Ge)-photoelastic modulator (ZnSe) mated optic pair (POL-PEM, (Polarizer-Photoelastic Modulator) mounted on a computer controlled precision rotary stage) which is positioned to intercept [ . . . L1:L2 . . . $]_{transmit}$ just after that beam-train exits OSD 100. Systems further comprise another PEM-POL pair (also mounted on a precision computer controlled rotary stage) to intercept the backscattered radiance of the incident beams in the sensor's collector-receiver. (The optical order of linear polarizer and photoelastic modulation optics is reversed in the collector-receiver.) The POL-PEM:PEM-POL (transmitter:receiver) optical group or photopolarimeter with laser source beams L1 and L2 is called a Mueller matrix spectrometer (MMS) (not illustrated). The integrated electro-optic/optomechanical apparatus and ancillary electronics, together with the software subsystems described below is referred to as a DIAMMS Photopolarimetric lidar standoff detection system.

An MIR detector D (also not illustrated) is positioned at the focus of the MMS receiver. Detector D preferably comprises a liquid $N_2$ cooled HgCdTe semiconductor detector chip (1×1 $mm^2$, typically). The detector D produces a photocurrent referred to as a scattergram, provided that both ZnSe crystals of MMS are under active (and proper) transduction via their respective tensor (T) PEM circuits. This scattergram product manifests an intensity modulation of the form $$I_{ac}=I_{dc}+I_{ac}(n\omega_1,k\omega_2,n\omega_1\pm k\omega_2)$$

to first-order in its Fourier (frequency) space; where $I_{dc}$ is a scalar amplitude that is phase insensitive and tracks the [1,1] element of M, and $\omega_1$ and $\omega_2$ are the transmitter and receiver PEM driver frequencies, respectively, that tag the other 15 phase-sensitive M-elements. PEM driver frequencies $\omega_1$, $\omega_2$ are offset by a few KHz. In the above expression for $I_{ac}$, only the primary and first-order harmonic terms n, k=integers 1 and 2 are typically used. (Harmonics greater than 100 KHz are naturally attenuated by Bessel coefficients in the scattergram function and, may also be suppressed by electronic filtration, if necessary.) The altering vector (phase sensitive) component of the scattergram, namely function $I_{ac}$, is thus represented by a sum of discrete primary and harmonic terms: $\omega_1$, $\omega_2$, $2\omega_1$, $2\omega_2$, $\omega_1\pm\omega_2$, $\omega_1\pm2\omega_2$, $2\omega_1\pm\omega_2$, $2\omega_1\pm2\omega_2$; where each frequency tags one non-[1,1] M-element. Meanwhile, the direct scalar (phase insensitive) term of scattergram, $I_{dc}$, corresponds precisely to element $M_{11}$ and vice versa. Determination of M is thus equivalent to measurement of coefficients of primary and overtone frequency component throughputs of $I_{ac}$. These measurements may be performed via discrete phase-sensitive detectors tuned to frequencies $\omega_1$, $\omega_2$, $2\omega_1$, $2\omega_2$, $\omega_1\pm\omega_2$, $\omega_1\pm2\omega_2$, $2\omega_1\pm\omega_2$, $2\omega_1\pm\omega_2$; plus an additional single-channel measurement for $I_{dc}$, whereby the scattergram is chopped far below the least PEM driver frequency (at ~4 Hz, for example) and filtered through a separate lock-in amplification channel.

In embodiments according to the present invention, a digital data acquisition system is preferred for acquiring all elements $M_{ij}$ as such, directly from the full temporal scattergram waveform (I). The digital data acquisition system preferably includes a high-speed serial vector network analyzer that samples I at 800 KHz or beyond (to eliminate aliasing).

There are 15 modulo 2 normalized differential M-elements $\{\underline{\Delta M_{ij}}\}=[M'_{i,j}(\lambda_{on})/M'_{1,1}(\lambda_{on})-M_{i,j}(\lambda_{off})/M_{1,1}(\lambda_{off})]$ produced by the photopolarimeter, with the photopolarimetric lidar's switched-beams transmit and received wave-trains [ . . . L1:L2 . . . ]; where $M'_{i,j}$ and $M_{i,j}$ designate the Mueller elements on-resonance (analytic beam L1) and off-resonance (reference beam L2) of analyte; respectively, and $i,j^{TM}1,2,3,4\neq1,1$. A sample of these data sets for select crystalline amino acids and sugar compounds in wafer form—the building blocks of proteins and precursors of biological warfare agents that the photopolarimetric lidar must ultimately detect, is provided in Table 3 of the '701 patent.

Success in identifying the chemical-biological (CB) target S, via pattern recognition from these DIAMMS data sets, requires mapping at least one (normalized) susceptible member element, from the full field of 15 in $\{\underline{\Delta M_{ij}}\}$, onto the target S with sufficient signal-to-noise ratio. The detection uniqueness picture becomes clearer, however, when more of the available 15-member $\{\underline{\Delta M_{ij}}\}$ DIAMMS elements show susceptible behavior to target (analyte, CB agent/simulant, contaminant, and target are synonymous) as prompted by the polarization-modulated probe beams $[\ldots L\mathbf{1}{:}L\mathbf{2}\ldots]_{transmit}$ causing the excite-then-relax molecular vibration activity in targeted molecules.

Several neural network models were built and trained-validated-tested against susceptible $\{\Delta M_{ij}\}$ elements in the analyte's unique Mueller-domain space. Repeated training of a best-performance network model yielded an optimum weight matrix product. This weight matrix is essentially a collection of all parallel interneuron strengths between architectural layers of the network, and, may be deployed in the photopolarimetric lidar system as a passive pattern recognition filter accordingly. In particular, any mapping of real-time preprocessed DIAMMS data fed through the neural network's weight matrix and onto the Mueller domain-space of analyte would cue an alarm condition against that analytic compound. Some target CBs will need less than all differential-absorption Mueller matrix elements to be identified. Embodiments of systems according to the present invention may be configured to extract only those elements needed to identify certain target CBs.

In general, OSD 100 interfaces to a robust networked computer host system via standard I/O interfaces, such as a pair of RS-232 serial ports, SP1 and SP3 (not illustrated), which are positioned on an electronics expansion box (not illustrated) supporting bidirectional computer ↔OSD 100 data transfers. SP1 and SP3 provide status and control that monitor and control a series of precision, logical, translation and shunted actions on flat infrared mirror optics inside OSD 100, as described below. Although RS-232 interfaces are employed in this embodiment, other communications protocols and interfaces such as USB, RS-485, RS422, IEEE1394, Firewire, Ethernet, WiFi, and the like, may be implemented in alternative embodiments.

FIGS. 1*a*-1*d* and 2*a*-2*d* show schematic and perspective representations, respectively of a preferred embodiment of an optomechanical switching device according to the present invention. OSD 100 has several modes of operation: (a) a wavelength calibration mode called Case W1, where beam L1 is tuned to an absorption peak of backscattering target (analytic wavelength); (b) a wavelength calibration mode called Case W2, where beam L2 is tuned off the absorption peak of backscattering target (reference wavelength), other IR vibrational modes of analyte, and any interferent scatterer—while still in the closest possible proximity to the wavelength of L1; (c) a data collection mode called Case MM1, where the M-elements at beam wavelength L1 are acquired (analytic beam)—while beam L2 is monitored (reference beam); (d) a data collection mode called Case MM2, where the M-elements at beam wavelength L2 are acquired—while beam L1 is monitored; and (e) a failsafe or safe park mode that is activated on start-up and whenever a fault in photopolarimetric lidar system operations is detected called Case FSI, where both beams L1 and L2 are confined and terminated.

As shown in FIGS. 1*a*-1*d* and 2*a*-2*e*, a preferred embodiment of an OSD 100 includes a housing 102 that provides an optically sealed enclosure through which there are provided a number of input and output ports for passage of MIR light. Housing 102 is preferably cube shaped and orthogonal and substantially rigid inner surfaces to enable mounting and precision alignment of optical elements, actuators and related components. In the preferred embodiment housing 102 is constructed of a material such as black-anodized aluminum, or plexiglass—which is opaque in the MIR range and is also transparent to visible light so that the operation and alignment of internal components can be observed. OSD 100 includes an output port (not illustrated) that provides an optical path to a beam terminator 114 and an output port (also not illustrated) that provides an optical path to a power detector head 104. Beam terminator 110 is an energy absorbing terminator for incident beam L1, beam terminator 112 is an energy absorbing terminator for incident beam L2 and beam terminator 114 is an energy absorbing terminator for L1 and L2. Translation stage 134 is a rectilinear translation stage driven by stepper motor 136 and connected to a controller/indexer unit such as a Daedal model MC2000 controller/indexer unit with encoder (not shown).

Ports 138 and 140 are input ports for laser beams L1 and L2, respectively; port 142 and 144 are output ports for terminating beams L1 and L2 into energy absorbing terminators (also called "beam dumps") Beam terminator 110 and beam terminator 112 via mirrors mirror 122 and mirror 118, respectively; ports 150 and 154 are output ports for directing beams L1 and L2 into optical spectrum analyzers 146 and 148 external to OSD 100 via mirrors 128 mirror 126 and mirror 130, and mirror 124, respectively. Port 152 is an output port for directing beams L1 or L2 on an optical axis toward a suspect target (S) via linearly indexed mirror 128 or 130, through a quarter-wave plate retarder 156, then through transmitter POL-PEM (external to OSD 100 and not illustrated). Power detector head 104 is positioned on axis above a beam splitter 116, which is a coated optic that reflects roughly 4% of an incident beam at 90° and transmits the rest; armatures 162, 164 and 166, are mechanical actuators that fold infrared flat mirrors 122, mirror 118, and 120, in and out of beam paths L1 into beam terminator 110, L2 into beam terminator 112, and L1 or L2 into beam terminator 114, respectively. Translation stage 134 is a rectilinear translation stage controlling the mirror cradle 132 carries linearly indexed mirrors 128 and 130 driven by stepper motor 136 connected to controller/indexer unit with encoder. Stepper motor 136 precisely moves translation stage 134 and mirror cradle 132 mounted thereon, together with attached mirrors 128 and 130 by a number of small indexed steps.

Figure 1B:
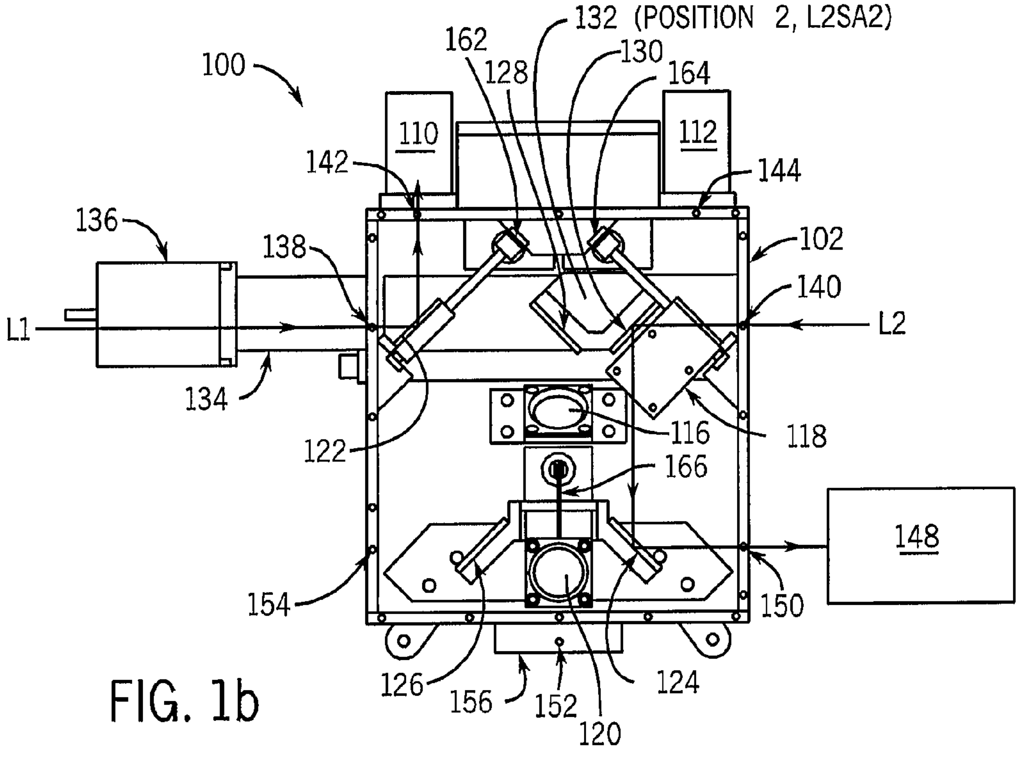
FIG. 1*b* is a top schematic view (with top plate removed) of the preferred embodiment of an Optical Switching Device according to the present invention in a second position/configuration.
Figure 1C:
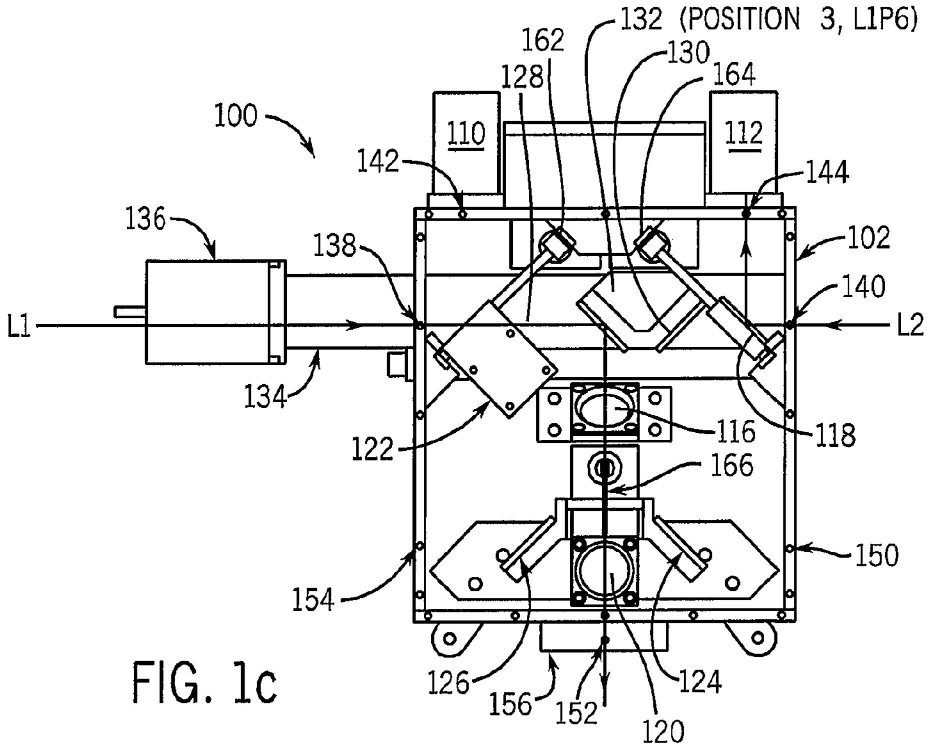
FIG. 1*c* is a top schematic view (with top plate removed) of the preferred embodiment of an Optical Switching Device according to the present invention in a third position/configuration.
Figure 1D:
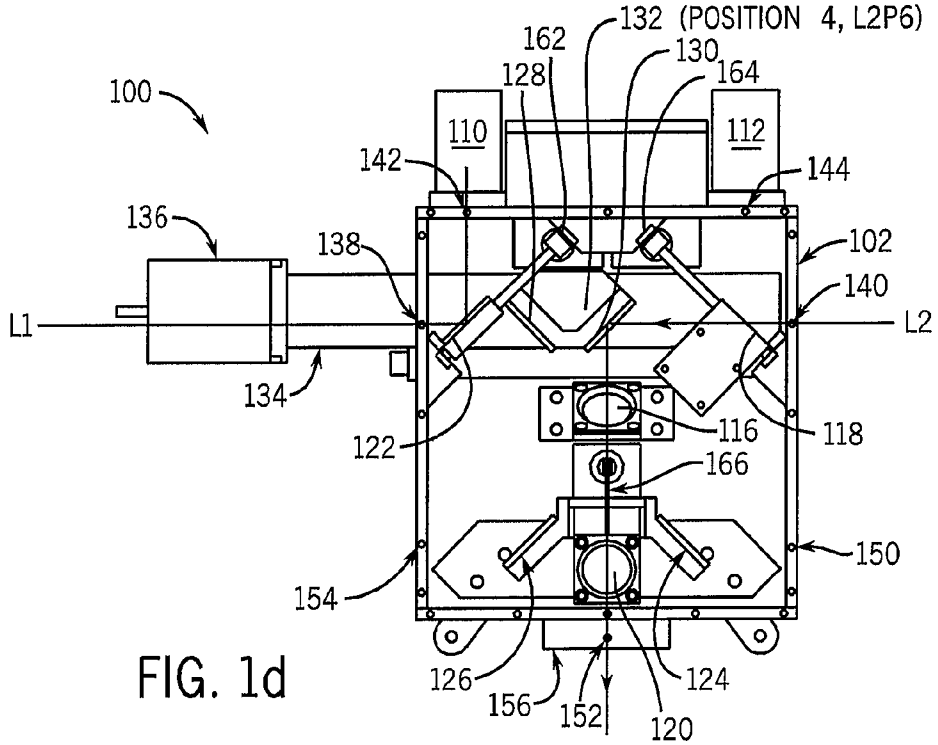
FIG. 1*d* is a top schematic view (with top plate removed) of the preferred embodiment of an Optical Switching Device according to the present invention in a fourth position/configuration.
Figure 2A:
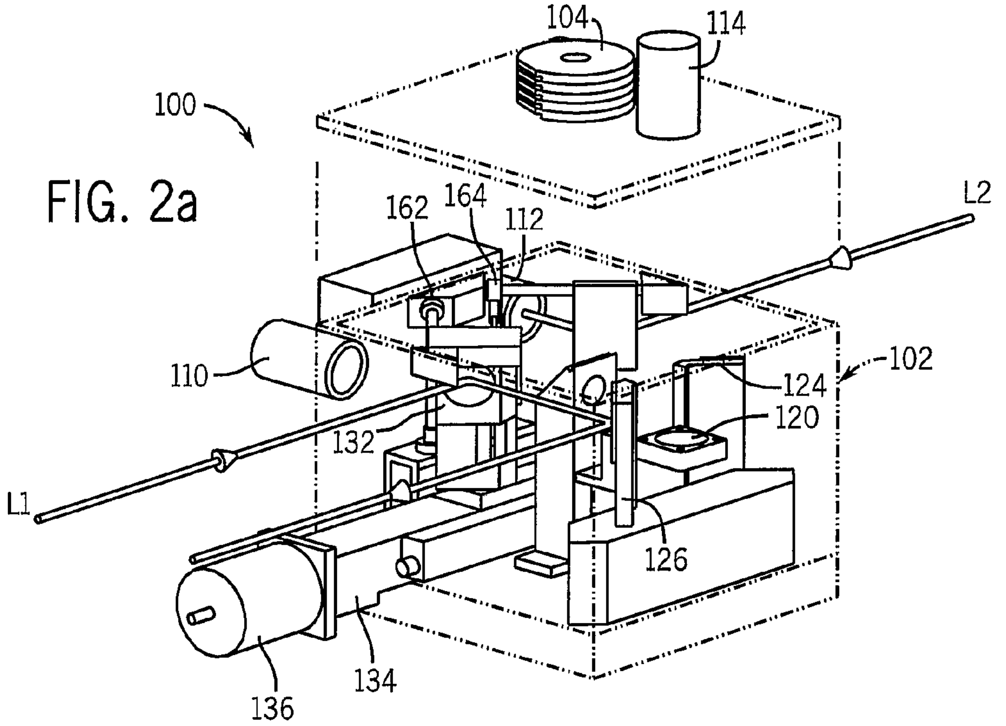
FIG. 2*a* is a perspective view of the preferred embodiment of an Optical Switching Device according to the present invention in the first position/configuration shown in FIG. 1*a*.
Figure 2B:
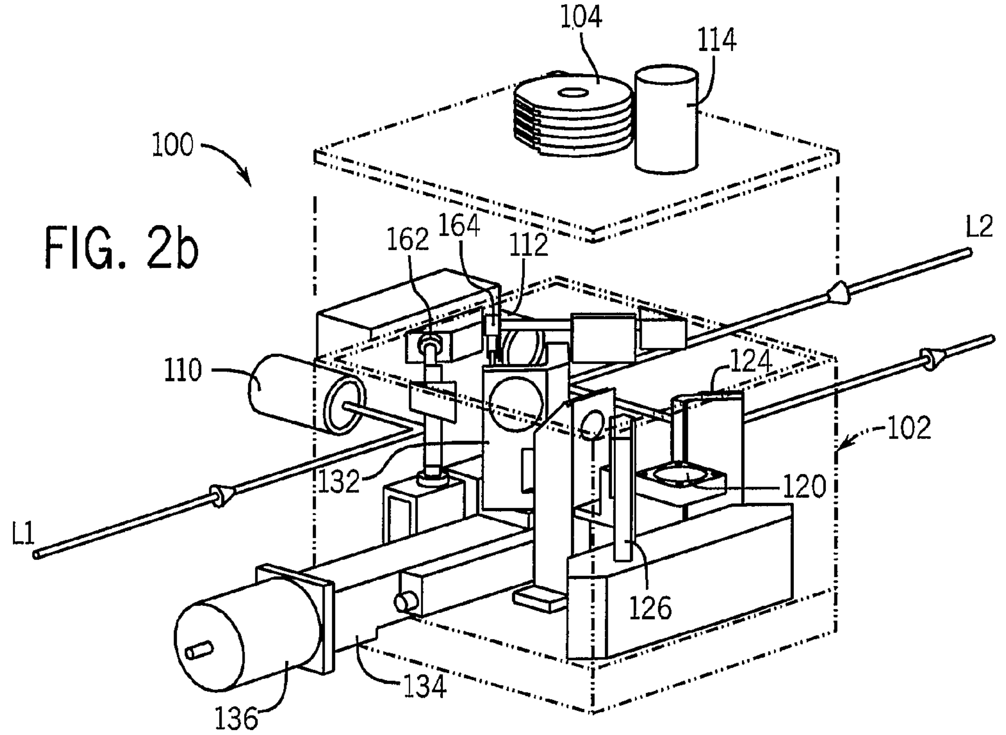
FIG. 2*b* is a perspective view of the preferred embodiment of an Optical Switching Device according to the present invention in the second position/configuration shown in FIG. 1*b*.
Figure 2C:
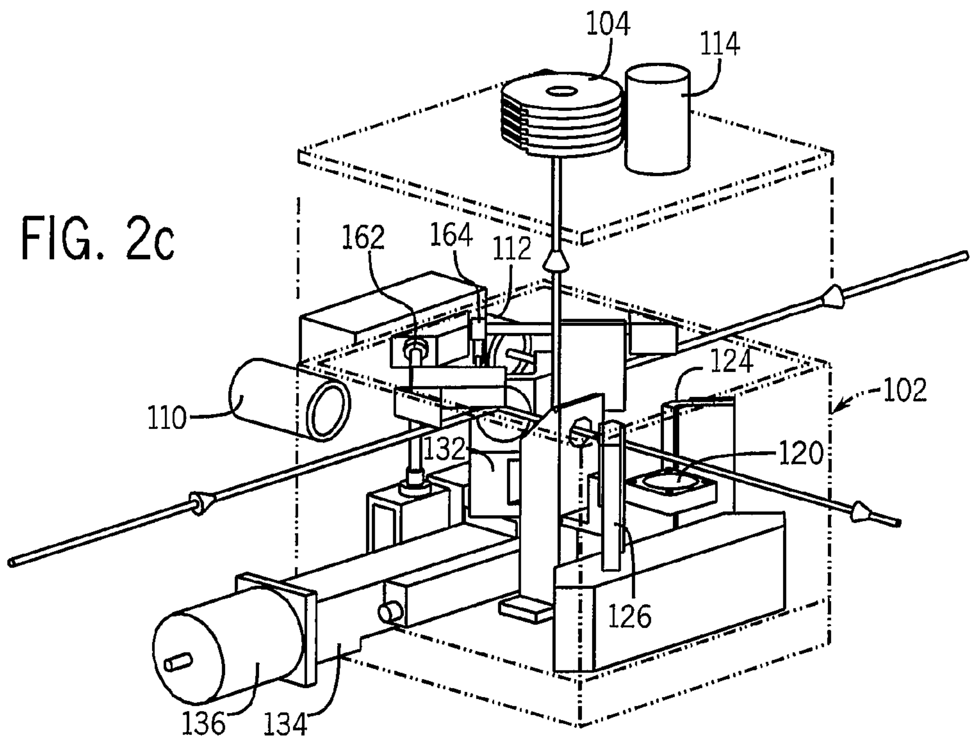
FIG. 2*c* is perspective view of the preferred embodiment of an Optical Switching Device according to the present invention in the third position/configuration shown in FIG. 1*c*.
Figure 2D:
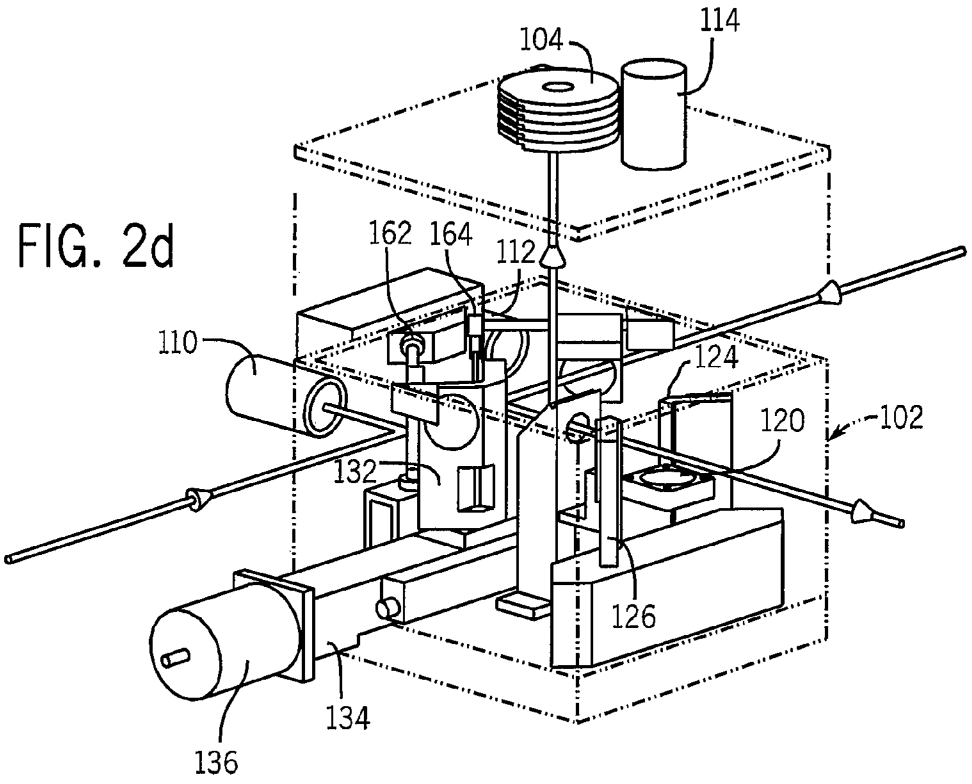
FIG. 2*d* is a perspective view of the preferred embodiment of an Optical Switching Device according to the present invention in the fourth position/configuration shown in FIG. 1*d*.
Figure 2E:
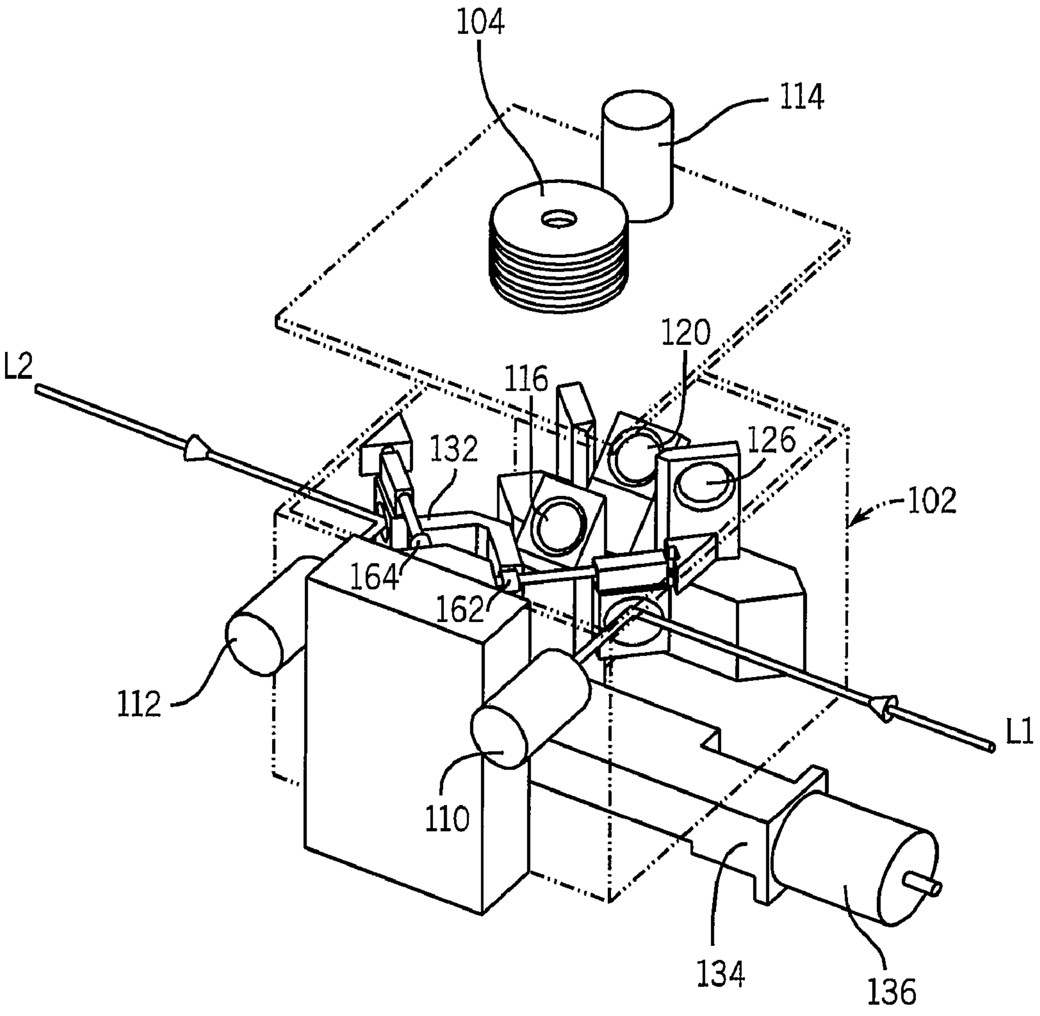
FIG. 2*e* is a perspective view of the preferred embodiment of an Optical Switching Device according to the present invention in a failsafe position/configuration.

FIG. 2*e* shows a failsafe configuration of OSD 100 enacted on startup of the sensor, and whenever a fault condition is detected. The 2-dimensional schematics of FIGS. 1*a*-1*d* and 2*a*-2*d* depict basic protocols for acquiring differential-absorption Mueller matrix spectroscopy (DIAMMS) data sets as described below.

Positional status information from all moving optics is continuously updated by obtaining data from proximity sensors and mechanical switches integrated with or attached to armatures 164, 166 and 162, and to translation stage 134 controlled by stepper motor 136 and its associated driver electronics. This status feature of OSD 100 rapidly senses fault conditions in the running configuration of the photopolarimetric lidar system and sets a flag related to the fault condition. Should a flag be set, the current photopolarimetric lidar system operation will pause. An operator is then alerted and informed of the fault situation via a coded string or a message displayed on a computer screen. Appropriate input to correct the fault by the operator resets this flag, and switching operations may commence after satisfactory systems checks are concluded. Fault conditions typically include detection of misaligned internal stationary optics, stray moving optics, and/or disorders external to OSD 100 such as laser cavity overheating, beam instability, power disruption, etc.

Embodiments of the present invention preferably include software. Such software is stored on a computer-readable medium which may include an electronic, magnetic, optical, or other physical device or means that can contain or store a computer program for use by or in connection with a computer-related system or method executable on a personal computer. The software may comprise one or more separate programs. The personal computer may incorporate one or more processors, memory, and I/O devices that are communicatively coupled via wired or wireless (wifi) interfaces to peripheral devices. Such peripheral devices perform operations to synchronize and automate the operation of a photopolarimetric lidar system including (i) photopolarimeter beam switching functions carried out by an OSD 100, including control, automation, and photopolarimeter maintenance; MMS optical configuration protocols; (iii) photopolarimetric lidar system scattergram acquisition-preprocessing operations; and (iv) neural network pattern recognition decision-making. The software also preferably includes a graphical user interface to accept input data from an operator and to display system status and output results.

In the preferred embodiment according to the present invention, menu scripts from compiled C++ software modules are used to handle OSD 100 control, automation, and photopolarimeter maintenance. Specifically, widgets are displayed on the computer to facilitate: (1) calibration and self-alignment of MMS transmitter; (2) logistics that maintain integrity of switching of beams and dwell timing of wave-train; and (3) vigilant failsafe operating mode status, i.e., the OSD 100 actuator and controller will dump beams L1 and L2 into appropriate beam terminators whenever an interrupt or error status is triggered by one or several OSD 100 proximity sensors.

The infrared beams L1 and L2 are preferably generated by waveguide cavities containing standard and isotopic $CO_2$ continuous wave (cw) laser systems (such as the Coherent GEM Select-50) with Brewster windows to provide horizontally-polarized outputs. While other types of lasers may be employed, the $CO_2$ laser is preferred because of its efficiency in the mid-IR range. Beams L1 and L2 are directed through multiple ports 138, 142, 144, 140, 150, 152 and 154 of OSD 100 as illustrated in FIGS. 1*a*-1*d* and FIGS. 2*a*-2*e*. Ports 138, 142, 144, 140, 150, 152 and 154 preferably provide 9.5 mm diameter clear apertures. Output ports are also provided (but not specifically illustrated) for directing beams to beam terminator 114 and power detector head 104. Other input/output ports may also be provided in OSD 100, as needed. Traffic through all input/output ports may be controlled by systematic electro-mechanical actions that move folded optical mirrors 118, 120, and 122, and linearly-indexed mirrors 128 and 130 into and out of alignment with beams L1 and L2 in conjunction with stationary mirrors 124 and 126. Although a variety of mirrors of different sizes and types may be employed, in alternative embodiments infrared mirrors residing inside OSD 100 according to the present invention are preferably 25.4 mm diameter and 1/10 wave flat.

Stationary beam splitter 116 deflects a small percentage (preferably 4% reflectance with anti-reflection coatings on both surfaces) of L1 or L2, sent to target surface S, for power monitoring. Power monitoring takes place continuously whenever L1 and L2 are energized. The energy of beam L2 is required to be close to that of L1 yet outside that absorption band of analyte for which L1 was tuned. Moreover, by definition, the energy of reference beam L2 should be exclusive of other resonance vibrational bands of the targeted analyte for detection or any sharp absorption moiety by an interferent scatterer that partially comprises mass S inside the irradiating beam's cross-section.

Choreography of switching modes in the preferred embodiment according to the present invention, as illustrated in FIGS. 1*a*-1*d* and 2*a*-2*e* is discussed next.

In DIAMMS measurement protocols according to the present invention, analytic beam L1 is tuned in wavelength to match a peak absorption band exhibited by the CB aerosol/surface contaminant (i.e., the analyte present at the beam-targeted surface S) under irradiation. In general, the wavelength lies in the range of 9.1-12.1 μm. Tuning is performed by gratings within the $CO_2$ laser using P- and R-branch transitional assignments. Amplitude-stabilization of the beam via inspection of its power at power detector head 104 (e.g., FIG. 2*e*) follows.

FIGS. 1*a* and 2*a* show schematic and perspective representations, respectively, of a wavelength calibration and selection mode of OSD 100, referred to as Case W1. In Case W1, beam L1 enters OSD 100 through port 138, is reflected 90° by mirror 128 in the exact position as shown in FIG. 1*a* (Position 1 (L1SA1) of mirror cradle 132), is reflected another 90° by stationary mirror 126, exits OSD 100 parallel to entering it through Port 154, and subsequently passes into an external optical spectrum analyzer 146. In spectrum analyzer 146 the beam's E-field is diffracted and its orders of diffraction are projected onto a florescent screen detector calibrated to the lasers' branch-transitional assignments. That wavelength value is then entered into computer memory and utilized later in M-data collection modes of the sensor protocol, described below. Meanwhile, reference beam L2 enters OSD 100 through port 140, is reflected 90° by folding optical mirror 118 (folded up 45° by armature 164), sent through Port 144, and terminated inside beam terminator 112.

FIGS. 1*b* and 2*b* show the OSD's 100 second calibration and wavelength mode called Case W2. This configuration is established when mirror 118 is folded down and out of the path of beam L2 by actuating armature 164 to rotate mirror 118 down, thus allowing mirror 130 to intercept L2 after stepper-motor 136 indexes the rectilinear translation stage 134 of mirror cradle 132 into position 2 (L2SA2) (FIGS. 1*b* and 2*b*). Reference beam L2 is thereby reflected downward 90°, reflected again 90° by stationary mirror 124, and terminated inside spectrum analyzer 148, while analytic beam L1 is dumped into beam terminator 110 via a 90° reflection by mirror 122 after the actuation (rotate up) of armature 162. The wavelength value of L2, projected onto the florescent screen of spectrum analyzer 148, is likewise recorded and stored into computer memory for later use in the M-data collection modes of the photopolarimetric lidar system. As in Case W1, L2 in Case W2 must also be stabilized in power before proceeding to the Mueller data collection modes discussed next.

FIGS. 1*c* and 2*c* depict the M-elements measurement mode of OSD 100 for analytic probe beam L1 (resonance-tuned) referred to herein as Case MM1. In general, an evanescent wave traverses the contaminant/analyte surface to which the beam is incident, due to absorption of the field energy of the resonance-tuned beam via the imaginary part of complex refractive index $N(\lambda)=\eta(\lambda)+i\xi(\lambda)$, with $i\xi(\lambda)\neq 0$. This boundary condition will be manifest in the full M-elements measurement. To configure the OSD 100 for Case MM1, mirror carriage 132 translates on translation stage 134 to position 3 (L1P6) as shown in FIGS. 1*c* and 2*c*. Armature 162 positions mirror 122 out of the path of L1 and armature 164 positions mirror 118 into the path of L2. L2 is directed to beam terminator 112 and terminated after transmission through Port 144. L1 is directed by mirror 128 (mounted on mirror cradle 132) through beam splitter 116 (where a portion of the beam is deflected to power detector head 104 for monitoring the beam's power) and to port 152 where it exits. As it exits through port 152, L1 passes through a retarder 156, preferably a 1.4 cm clear aperture quarter-wave plate Fresnel Rhomb (II-VI, Inc., FRZ-9-11.5-0.55-O-IR). Retarder 156 converts horizontal polarization into circular polarization. The circularly polarized L1 next traverses the POL-PEM optical pair of the MMS transmitter. Optic POL converts circular polarization of L1 to a linear polarization state, passing that beam to the PEM optic, where the E-field of L1 is oriented 45° to the ZnSe crystal axis (PEM). The transducer frequency, driving this transmitter PEM, is $\omega_1$=37 KHz. Incident beam L1 is then directed to the backscattering target S in object space; i.e., the distant area or volume suspected of containing CB contaminant.

Backscattered radiance emanating from the irradiated area/volume comprising S is collected over a wide-aperture field-of-view, collimated, and then reduced 10× via the photopolarimetric lidar system receiver's Cassegrain beam-condenser unit, 25.4 cm primary aperture. This condensed-collimated beam radiance, emanating from S, is then polarization-modulated a second time at frequency $\omega_2$=39 KHz as it passes through the receiver ZnSe modulating optic (PEM) and converted back into a linear polarization state after traversing the attached POL optic. The POL of this mated receiver (PEM-POL) optical pair effectively modulates the intensity $|E|^2$ of the exiting laser beams' backscattered radiances at the photopolarimetric lidar system's photoconductive detector chip surface, and the subsequent electronic acquisition of scattergrams is performed. Driving the PEMs at these modulation frequencies allows the measurement of 9 independent Mueller matrix elements in the home POL-PEM:PEM-POL orientation of Mueller matrix spectrometer (MMS). The home position is defined by the horizontal axis of linear polarization in both POL optics (they are mounted 45° to their respective PEM optic). The remaining non-degenerate M-elements may be obtained by permuting the MMS's POL-PEM:PEM-POL optical configuration three separate and distinct times from its original (home) optical configuration (position) in this sequence: clockwise 45° in the receiver PEM-POL optical group; clockwise 45° in the receiver POL-PEM optical group; and finally counter-clockwise 45° in the transmitter POL-PEM optical group.

A peak retardation of $\delta_0$=2.404 radians by both transmitter and receiver PEMs—for each wavelength of L1 and L2—facilitates the separation of distinct Mueller element assignments in the total intensity of scattergram (I) of backscattered radiation recorded at the sensor's photoconductive chip, and the subsequent extraction of M-elements from this scattergram I.

FIGS. 1*d* and 2*d* depict the reference beam M-elements measurement mode of OSD 100 referred to herein as Case MM2. In Case MM2, L2 is allowed to probe the analyte surface. Since L2 is detuned off the molecular vibrational resonance band of the target CB analyte(s) there is no absorption and thus nil evanescence by the incident beam at the air-analyte boundary; i.e., refractive index $N=\eta(\lambda)>0$, with the imaginary part $i\xi(\lambda)=0$. However, L2 will experience a phase change of $\pi$ from the low-to-high refractive index (air-to-analyte) and 0 phase change from the high-to-low refractive index (analyte-to-air) by a purely refractive medium. These boundary conditions will also be manifest in the full M-elements measurement.

To configure the OSD 100 for Case MM2 mode, mirror cradle 132 translates on translation stage 134 to Position 4 (L2P6), as shown in FIGS. 1*d* and 2*d*. Armature 162 positions mirror 122 into the path of L1 for beam termination through 142 into beam terminator 110 and armature 164 positions mirror 118 out of the path of L2 allowing L2 to pass through to indexed mirror 130. L2 is directed by mirror 130 through beam splitter 116 (where a portion of the beam is deflected to power detector head 104 for power measurement) and to port 152 where it exits through retarder 156 which converts horizontal polarization into circular polarization. The circularly polarized L2 traverses the POL-PEM optical pair of the MMS transmitter and passes onward into object space to backscatterer S.

The backscattering M-elements at this reference wavelength of beam L2 are acquired in the same way as in Case MM1. Recall that $\delta_0$=2.404 in MMS transmitter and receiver PEMs must be maintained between switched beams L1 and L2. Because L1 and L2 are at different wavelengths, some tuning is generally required to maintain $\delta_0$. This is provided through a feedback loop mechanism, with inputs from each of the PEM phase-controller circuits. These data, together with the M-elements measured on-resonance from Case MM1, are stored into computer memory and recalled for construction of the important Mueller detection domain of targeted analytic backscatterer S.

FIG. 2*e* shows OSD 100 in a Safe Park or failsafe mode referred to herein as Case FSI. In Case FSI L1 and L2 are dumped into beam terminator 112 and beam terminator 114 via armatures 164 and 166 producing the configurations of mirror 118 and mirror 120, as shown. Note that a small percentage (4%) of L1 is sent to power detector head 104 via beam splitter 116 front optical surface. Monitoring of beam L1, while the OSD 100 is safely parked, alerts the polarization photopolarimetric lidar system operator of a 'live-beam' status. It also allows the operator to check for power stabilization of beams' in the system initialization process. The analogous situation of dumping L1 into beam terminator 110, L2 into beam terminator 114, and monitoring power of beam L2 at power detector head 104 is accomplished by the proper permutations of armature 162, 164 and of indexed translation of mirror cradle 132.

Another aspect of this embodiment involves OSD 100 automation and control in relation to sensor protocols, processing the photopolarimetric lidar system's data output product, and providing CB alarms or other end results. A computer platform serves these important functions: OSD 100 electro-mechanical switching of beams; permutation of configurations of MMS (POL-PEM:PEM-POL); DIAMMS data acquisition (gated scattergram acquisition-preprocessing); alarms (neural network pattern recognition per Ref. 12); and other ancillary operations.

Computer Command and Control System

A computer command and control ($C^3$) system to meet the needs of embodiments according to the present invention preferably include dual-tiered mother boards (800 MHz bus) each supporting an Intel Pentium-4 CPU (3 GHz), Cache (1 MB) and Double Data Rate Memory (512 MB at 400 MHz), USB 2.0 ports, IEEE 1394 Firewire, Ethernet 10/100 ports; and ATA133 MHz Western Digital Caviar hard drives (20 GB). Microsoft XP Professional Service Pack 2, Visual Studios 2005, and C++ (Version 6.0) are operating system, programming environment, and code-development language, respectively. Remote communications between the polarization lidar and computer are conducted via a Local Area Network (LAN), which is accessible via a 2.4 GHz 54 Mbps wireless broadband router. In particular the use of a wireless network interface will facilitate deployment in the field of one or more remote tactical lidar systems operated by a computer, command and control ($C^3$) system positioned at a standoff distance. Other hardware and/or software platforms having at least comparable processing, memory and I/O capabilities may likewise be employed in alternative embodiments.

Graphical User Interface

Figure 3:
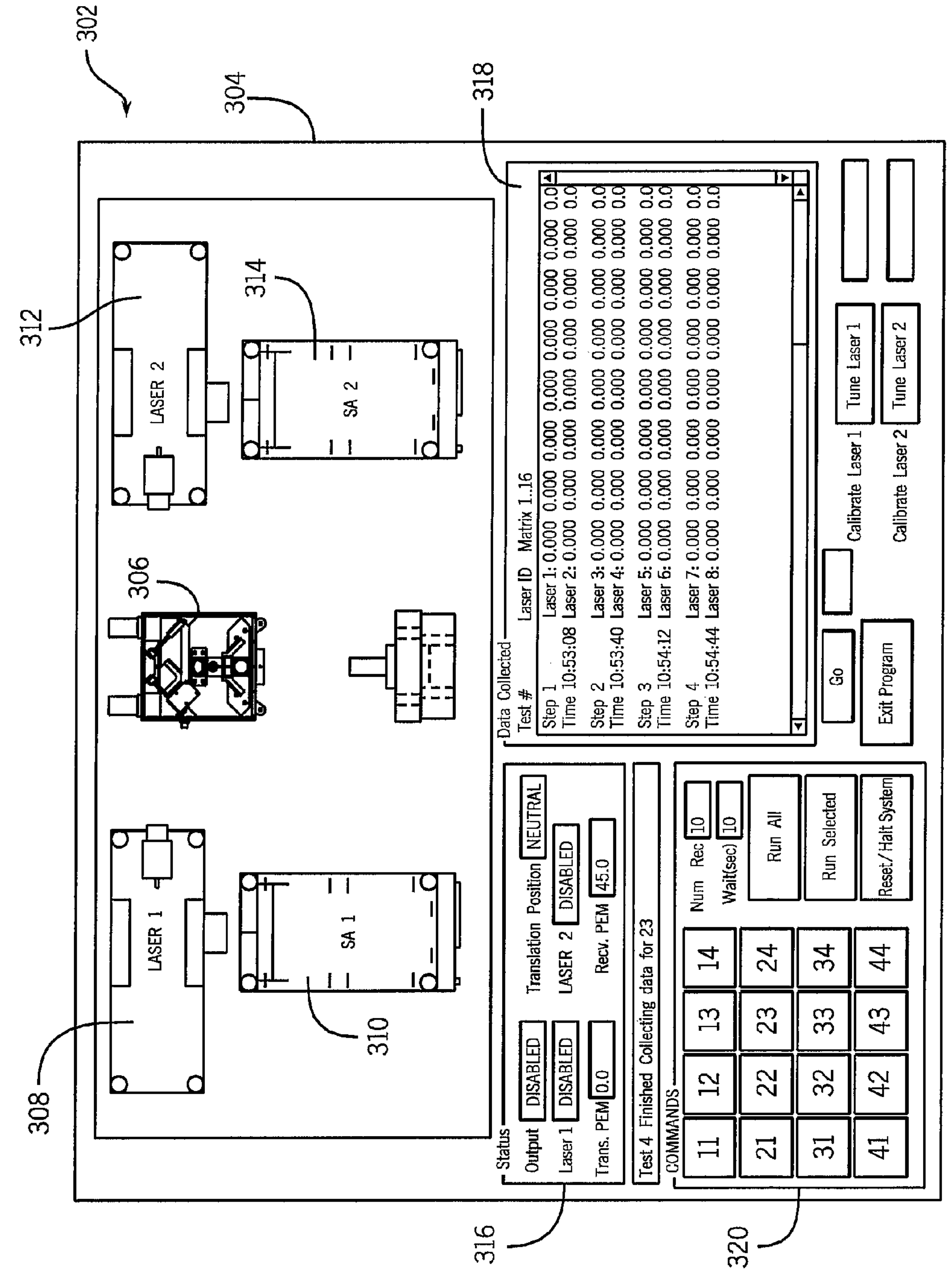
FIG. 3 shows a main graphical user interface of the preferred embodiment.

FIG. 3 depicts a Main Graphical User Interface (GUI) according to the preferred embodiment of the present invention. The overall GUI display 302 is preferably implemented in a graphical window. The GUI display window 302 includes the following: a top region 304 which may be implemented as a graphics box or as a separate window. Top region 304 displays a schematic drawing that includes icons of the main components of the photopolarimetric lidar system. In some embodiments, each icon may display substantially real time status information for the component it represents. In some other embodiments, additional details related to status and control of components may be accessed by double clicking on the respective icons. FIG. 3 shows an OSD 100 icon 306 at the center. An icon 308 for a laser 1 for generating L1 is positioned to the left of OSD icon 306 and an icon 310 for a first spectrum analyzer 146 is positioned beneath icon 308 for laser 1. An icon 312 for a laser 2 for generating L2 is positioned to the right of OSD icon 306 and an icon 314 for a second spectrum analyzer 148 is positioned beneath icon 312 for laser 2.

A second region 316 in the center of window 302 and to left, which may likewise be implemented as a graphics box or as a separate window, provides Status information including the following: beams' switching output ('Laser 1', 'Laser 2', 'Output'); location of mirror cradle 132 inside OSD 100 ('Translation Position'), and optical orientation of MMS transmitter-receiver POL-PEM:PEM-POL optics ('Trans. PEM' and 'Recv. PEM').

A third region 318 is defined in the lower left area of window 302: Region 318 monitors M-element measurement activity (console); selections per optical POL-PEM:PEM-POL orientation of Mueller matrix spectrometer (MMS, 4×4 array); waiting time per change of MMS orientation ('Wait [sec]'); number of M-elements currently measured ('Num Rec'); measurement options on collecting the 16 M-elements ('RUN ALL' 16 elements requires 4 MMS permutations of POL-PEM:PEM-POL optics) or a subset of elements ('RUN SELECTED', any combination of 4 optical permutations of POL-PEM:PEM-POL). Middle-right: interactive numerical data display console of M-elements at analytic (L1) and reference (L2) beams wavelengths with time stamps ('DATA COLLECTED', Cf, Cases MM1-MM2, (FIGS. 1*c*-1*d* and 2*c*-2*d*).

A fourth region 320 is defined in the Lower-right of GUI window 302. Fourth region 320 provides radio buttons for calibrating beams L1 ("Tune Laser 1") and L2 ("Tune Laser 2") to proper resonance-reference wavelengths (Cf, Cases W1-W2, FIGS. 1*a*-1*b* and 2*a*-2*b*), to start a measurement sequence ('GO'), and to end an experiment ('Exit Program').

Software Modules

Software modules are executed through dialog scripts as code objects. There are presently 8 functionality classes of C++ objects (coded modules/features, debugging, and re-optimization tasks are often updated) described as follows.

Figure 4:
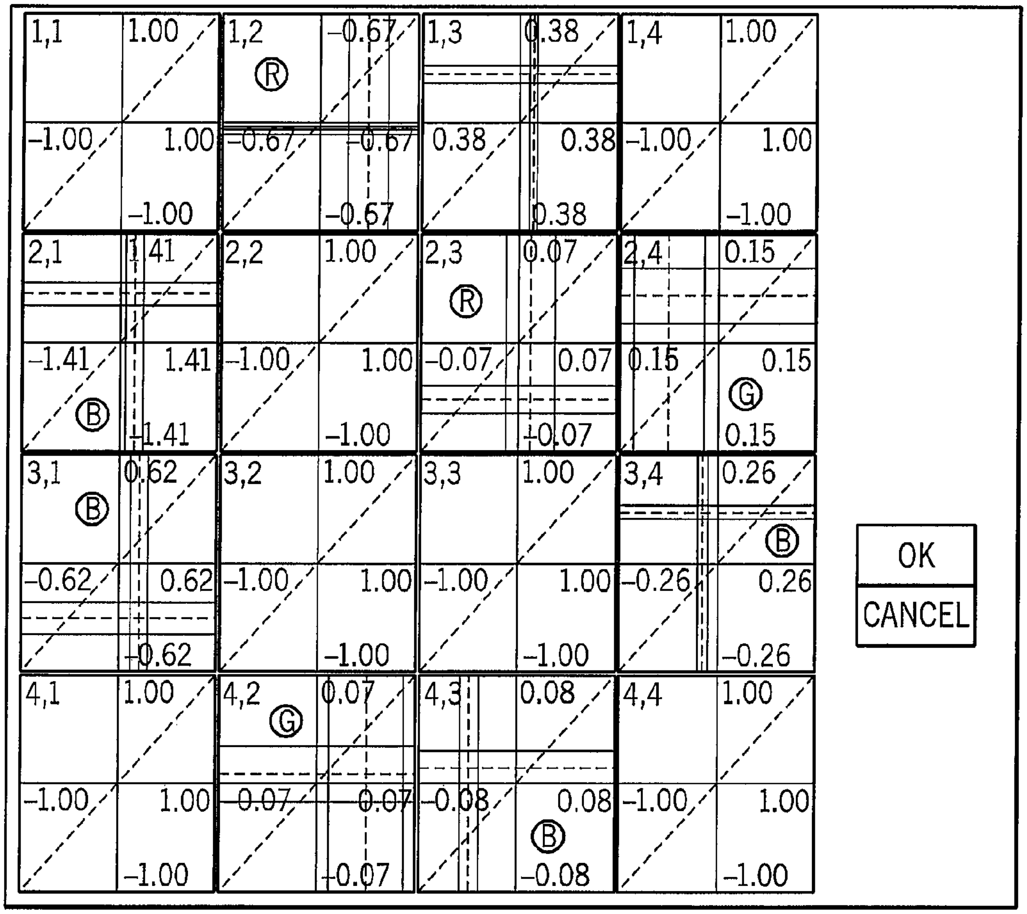
FIG. 4 shows a graphical display of data collected by a photopolarimetric lidar dual-beam switching device and Mueller matrix standoff detection system according to the present invention.

CDIAMMSApp. This class is the application file containing data objects used in construction of the main sensor dialog box CDIAMMSDlg. It manages overall OSD 100 operations, and generally all sensor operations, through a viewer with objects as shown in FIG. 4.

CDIAMMSDlg. This is the main sensor application class which spawns a 580 pixels high by 430 pixels wide GUI, that is managed via operator input options. Dialog corresponding to FIGS. 1*a*-2*a*, 1*b*-2*b*, and 2*e* protocol are open here with GUI updates, as are sequences of each M-elements measurement Cases MM1-MM2 corresponding to FIGS. 3 and 4. This class also portrays how the M-elements are presented in relation to parameters of the experimental run per FIG. 1*c*-2*c*. These objects include monitor/control status of the photopolarimetric lidar shutter system, as it is deployed for direct measurement of element $M_{11}$ (which involves the reciprocating mechanical shutter that chops backscattered radiances by laser beams L1 and L2 just before the lidar receiver's focal-plane HgCdTe detector chip), MMS transmit/receive POL-PEM:PEM-POL optical orientations (Four distinct orientations for both optic pairs are required for a complete measurement of the full 16-element Mueller matrix field), and the OSD 100 M-elements data collection modes of FIGS. 1*c*-2*c* and 1*d*-2*d*. Class CDIAMMSDlg is multi-threaded such that information in the GUI widgets (operator-to-lidar interface) is retained. This information is embedded in subroutines which control scattergram acquisitions, the M-elements processed from those scattergrams, and the individual M-elements graphical display. Safety precautions are also implemented in this class; e.g., it is forbidden to call calibration routines (Cases W1-W2, FIGS. 1*a*-2*a* and 1*b*-2*b*) when an M-elements measurement sequence is in progress (Cases MM1-MM2, FIGS. 1*c*-2*c* and 1*d*-2*d*). Furthermore, a state machine was incorporated herein that constantly monitors the running status of sensor and determines which GUI widgets to gray-out per operation mode of photopolarimeter. (The operator is prevented from accidentally triggering a faulty systems operation or initiating an unsafe/illogical sensor command.) Inputs from operator to GUI widgets are translated into objects, while command-reaction data flow is moderated by CDIAMMSDlg. For example, the OSD 100 operations as depicted in FIGS. 1*a*-1*d* and 2*a*-2*e* are scripted via CDIAMMSDlg, as is each of the MMS's four PEM-POL: PEM-POL permutations required for measurement of select M-elements, as discussed earlier. In the latter situation, suppose you are interested in measuring 6 of 16 M-elements. CDIAMMSDlg prompts the user to input those 6 elements of interest, and determines then executes the least of 4 PEM-POL:PEM-POL permutations necessary for measuring this subset of M. These data are then stored into files and graphed onto computer screen via class CMMatrixDlg, during the run of sensor if that is requested.

CSerialPort. This class is responsible for the initialization of communications (COM) between computer and OSD 100. Bus settings and management of bus ↔OSD 100 data I/O are conducted here. (Commands sent from all sensor code classes are passed through this bus, as are the accompanying responses.) This 'hand shaking' is moderated by a DSP controller external to the computer which parses data objects in select photopolarimeter operating modes.

DSPReader. This class assumes all behavior of the CSerialPort class (COM port of bus is set at 9600 BAUD, 8 bit, no parity, and one stop bit). It contains specific routines used to parse responses received from the DSP mentioned above.

CLaserComPort. This class is used to enable or disable the OSD 100 via DTR communications events, i.e., during wavelength-selection runs of photopolarimeter (Cases W1-W2, FIGS. 1*a*-1*b* and 2*a*-2*b*) calibration of polarization lidar data acquisition system, and data collection modes of MMS (Cases MM1-MM2, FIGS. 1*c*-2*c* and 1*d*-2*d*).

CStepperMotor. This class is used to encapsulate behavior of the stepper motor 136 component of OSD 100 (all Cases, FIGS. 1*a*-1*d* and 2*a*-2*e*). It communicates via a COM bus (8 bits, no parity, and 2 stop bits) and tracks the instantaneous position of mirrors 128 and 130, affixed to cradle 132, via stepper motor 136.

CLaserCalibrationDlg. This class, which is spawned from CDIAMMSDlg, is used to prompt laser beams L1 and L2 when the photopolarimeter is in calibration or wavelength-selection modes per FIGS. 1*a*-1*b* and 2*a*-2*b*, respectively. It produces a dialog box that allows tuning of each laser beam to an appropriate molecular resonance and non-resonance condition of analyte S (i.e., aerosol or surface contaminant). Upon execution of CLaserCalibrationDlg, a dialog box is presented whereby selecting wavelength (energy) of L1 (resonance-tuned) and L2 (reference-tuned) is facilitated. It presents a complete list of all allowable P- and R-branch transitional lines by the respective waveguide $CO_2$ (isotope and regular) laser. [Beam energies are grating-tuned and power-stabilized by the operator.] Wavelength (or beam energy) data entries are then stored in computer RAM for later sensor operation logistics (such as selecting sub M-elements per experimental run) and the labeling of measured data (from that run into a header).

CMMatrixDlg. This class constructs a layered GUI dialog box consisting of 16 individual panes representing each of the M-elements measured at the end of a test sequence (FIGS. 1*c*-1*d* and 2*c*-2*d*). This graphic of sixteen images, displaying all M-elements of backscatterer S, is 105×105 pixels high and wide and may be presented in real-time (concurrent to the current experimental run) or from archived data (images called from a database).

When executed by the sensor's computer network, coded modules (above) produce the GUI of FIG. 3 from which all OSD 100-DIAMMS operations are managed. The top half of screen (FIG. 3) depicts the DIAMMS transmitter section with OSD at center-top (see FIGS. 1*a*-1*d* and 2*a*-2*e*), POL-PEM at center-bottom, and lasers/spectrum analyzers to the sides. Activation of beams and status of OSD 100 optics is continually monitored at center-left of screen. Here, in the 'Output Enable/Disable' window, is where status of [ . . . L1:L2 . . . ] exiting the OSD 100, through output Port 9, is revealed (e.g., alert of current beam activity). The location of mirror cradle 132 inside the OSD 100 is revealed in radio button 'Translation Position,' while POL-PEM:PEM-POL orientation of MMS (Cases MM1 and MM2, FIGS. 1*b*-1*c* and 2*b*-2*c*) is inferred from 'Trans. PEM' and 'Rec. PEM' instrument buttons. The lower-left console of FIG. 3 provides information regarding: (1) status of an open experimental run (top bar window), (2) M-elements available for measurement per orientation of MMS; (3) waiting time per configuring a POL-PEM:PEM-POL orientation of MMS ('Wait' bar in seconds); (4) accumulative number of M-elements measured in current experimental run ('Num Rec' bar), (5) options on collecting elements in that run ('RUN ALL' implies all 16 elements will be collected, 4 optical permutations of POL-PEM:PEM-POL are required here); (6) sample data collection from 16 M-elements or a subset thereof ['Run Selected,' one or a combination of optical permutations of POL-PEM:PEM-POL (not to exceed 4) will result here]; and (7) means to halt experimental run (which puts the OSD 100 into park or failsafe mode FSI). The lower-right console of FIG. 3 shows a numerical display of M-elements data taken at both analytic (L1) and reference (L2) beam wavelengths with time stamps (Cases MM1-MM2). Finally, the lower-right panel of GUI, FIG. 3, portrays radio buttons for: calibration and tuning of beams L1 and L2 pertaining to Cases W1-W2 ('Tune Laser 1 and 2' to the molecular resonance and non-resonance wavelengths and stabilize); begin experiment ('Go'); and a graceful exit of experiment with return of optics to the MMS home position ('Exit Program').

In operation, a typical OSD 100 timing sequence enabling one dual-beam M-elements data collection cycle; i.e., production of 9 simultaneous matrix elements (i.e., the individual outputs of the sensor's 9-channel phase-sensitive data acquisition system (DAS) from 1 of 4 MMS configurations of POL-PEM:PEM-POL, is summarized in Table 2. The command "1 GH-5"[CR] [interpreted as 'GO HOME,' CR=carriage return], sent to OSD 100 via a microprocessor/microcontroller on a separate electronics board integrated into the sensor's DAS, translates mirror cradle 132 to its home or neutral optical position through bus SP3. (The translation stage 134 driving mirror cradle 132 is interfaced to a Deadal stepper motor controller 136, with encoder, FIGS. 1*a*-1*d* and 2*a*-2*e*.) Command "1D±214750[CR]" is interpreted as 'MOVE FORWARD (+) or BACKWARD (−)' a pre-select number of calibrated steps (214750) from mirror cradle 132's neutral or home position. Mirrors 128 and 130, on mirror cradle 132, intercept L1 and L2 beam paths, respectively, and place them on optical axis of port 108 toward the backscattering target S. The switching between beams, permutation of MMS, and collection of M-elements can be accomplished in as little 4 s.

TABLE 2

Collecting one set of 9 simultaneous Mueller matrix elements (M-elements) by the DIAMMS polarization lidar sensor system. Illustrated are those synchronized operations by the OSD, per FIGs. 2a-2e, that are conducted by systems software (see Section 3 of this paper).

| | Action | Computer Command | OSD Response |
|---|---|---|---|
| a | Safety failsafe mode | SP1, RTS Line = "OFF" | Case FSI, FIG. 2e, beams L1 or L2 confined/terminated/monitored. |
| b | Wavelength tuning of laser beams L1 and L2 | SP1, DTR = "OFF" | Causes control module to open. Folding of armatures 164, 162, indexing of mirror cradle 132, per Cases W1-W2, FIGs. 1a-1b and 2a-2b. |
| c | Initialize translation stage and mirror cradle 132 position | SP3, send command, "1GH-5[CR]" | Causes mirror cradle 132 to go to HOME position and register. |
| d | Select laser beam L1 for Mueller matrix measurement | SP3, send command, "1D+214750[CR] SP3, send command, "1D+214750[CR] | Causes mirror cradle 132 to align laser beam L1 on optical axis to scattering target. |
| e | Enable laser beam L1 output and enable output port 152 | SP1, RTS Line = "ON" | Causes the folding of armature 166 out of the path of L1 and exit of beam through port 152. |
| f | Collect Mueller matrix data at reference beam L1 wavelength | | First group of 9 simultaneous MMS elements per POL-PEM:PEM-POL optical orientation (Case MM1, FIGs. lc and 2c). |

TABLE 2-continued

Collecting one set of 9 simultaneous Mueller matrix elements (M-elements) by the DIAMMS polarization lidar sensor system. Illustrated are those synchronized operations by the OSD, per FIGs. 2a-2e, that are conducted by systems software (see Section 3 of this paper).

| | Action | Computer Command | OSD Response |
|---|---|---|---|
| g | Disable laser beam L1 and output port 152 | SP1, RTS = "OFF" | End Mueller matrix measurement for L1. Armature 162 folded into beam path dumping L1 into beam terminator 110, armature 166 blocks output port 152. |
| h | Initialize translation stage and mirror cradle 132 position | SP3, send command, "1GH-5[CR]" | Causes mirror cradle 132 to go to HOME position |
| i | Select laser beam L2 for Mueller matrix measurement | SP3, send command, "1D-214750[CR] SP3, send command, "1D-214750[CR] | Causes mirror cradle 132 to align laser beam L2 on optical axis to scattering target |
| j | Enable laser beam L2 output and enable output port 152 | SP1, RTS Line = "ON" | Causes the folding of armature 164 out of the path of L2 and exit of beam through port 152 |
| k | Collect Mueller matrix data at analytic beam L2 wavelength | | Same group of 9 simultaneous matrix elements as in step f (Case MM2, FIGs. 1d and 2d). |
| l | Disable laser beam L2 and terminate, disable output port 152 | SP1, RTS = "OFF" | End Mueller matrix measurement for L2. Armature 164 folded into beam path sending L2 to beam terminator 112, armature 166 is folded to block output port 152. |
| m | Safety failsafe mode | SP3, send command, "1D-214750[CR] | Case FSI, FIG. 2e, beams L1 or L2 confined/terminated/monitored. |

During this timeframe in which measurement of the 9 M-elements takes place, accuracy in the OSD 100 armature and reciprocated mirror cradle 132 movements discussed above must be maintained, and other functions mentioned above, external to OSD 100, that are dependent on its beam-switching action. These include maintaining the required $\delta_0=2.404$ phase-retardation of beams' through feedback by the PEM's controller circuits, the synchronous gating of scattergram streams into digital or analog data acquisition channels, the electronic transfer/storage of M-elements into computer memory, and the display of these data onto computer screen. Periods of dwell in beams [ . . . L1:L2 . . . ] may, however, last upwards of a few minutes to perhaps an hour for laboratory experiments where time-series acquisition of M-elements is desired or necessary. (When resolving the dynamic relationships of M-elements by aerosols disseminated inside a chamber, at lengthy time intervals, for instance.)

How data is presented from a typical DIAMMS run is portrayed in FIG. 4, where each sector of the 4×4 M array is populated via the 'Data Collected' portal 318, shown in the middle-right section of GUI 302. The coordinates (ordinate and abscissa) of all M-elements graphed, as shown, are inclusive of data set members $\{M'_{i,j}(\lambda_{on})/M'_{1,1}(\lambda_{on})\}$, $\{M_{i,j}(\lambda_{off})/M_{1,1}(\lambda_{off})\}$ For illustrative purposes, FIG. 4 displays the susceptible M-elements of crystalline mannose and a racemic mixture of tartaric acid (targets S). Size of the susceptible M-elements, as shown, is bounded by standard deviation on respective data set members: $\{M'_{i,j}(\lambda_{on})/M'_{1,1}(\lambda_{on})\}$ and $\{M_{i,j}(\lambda_{off})/M_{1,1}(\lambda_{off})\}$. Generally, in embodiments according to the present invention, these identification domain components with standard deviations (i.e., the intersection of horizontal and vertical solid lines in grids of FIG. 4) provide decreased area with increased precision of measurement, decreased accumulative error of photopolarimeter optics (i.e., alignment, and stability of PEMs), and increased signal-to-noise ratio in the sensor's detector element photoconductive HgCdTe chip with amplifier).

The centroid of each domain component (i.e., cross-hairs, FIG. 4) has coordinates $[<\{M'_{i,j}(\lambda_{on})/M'_{1,1}(\lambda_{on})\}>, <\{M_{i,j}(\lambda_{off})/M_{1,1}(\lambda_{off})\}>]$, where the bracketed entity < > refers to the time-averaged experimental value per set M-element measurement. Preferred selection rules for ascertaining an analyte's unique identification domain components are as follows.

Selection rules are used to assure distinctness in the same Mueller matrix element data sets, on-then-off molecular resonance beam backscattering from the analyte by [ . . . L1:L2 . . . ], as measured by the polarization lidar sensor. Selection Rule 1: $\{\underline{M}_{ij}\}\cap\{\underline{M}'_{ij}\}=\emptyset$. Select the same Mueller matrix element sets that move in opposite direction on-then-off molecular resonance beam backscattering from the analyte via [ . . . L1:L2 . . . ]; i.e., check for an anti-correlation coefficient between like data sets as, Selection Rule 2: $\{\underline{M}_{ij}\}\cdot\{\underline{M}'_{ij}\}<0$. Choose only those elements with coordinates $[\{M'_{i,j}(\lambda_{on})/M'_{1,1}(\lambda_{on})\}, M_{i,j}(\lambda_{off})/M_{1,1}(\lambda_{off})\}]$ that lie furthest from the diagonal line in Mueller space (i.e., the 45° line in each grid of FIG. 4) in the following manner, Selection Rule 3: $\{[\{<\underline{M}_{ij}>\}, \{<\underline{M}'_{ij}>\}]\forall i,j\in[1,2,3,4] \text{ s.t. } \rho\geqq\in\}$, where: the time average $<\underline{M}_{i,j}>=<M_{i,j}(\lambda_1)>/<M_{1,1}(\lambda_1)>$ is the on-resonance, normalized, backscattering Mueller element; $<\underline{M}'_{i,j}>=<M_{i,j}(\lambda_2)>/<M_{1,1}(\lambda_2)>$ is the off-resonance, normalized, backscattering Mueller element; c is an arbitrarily-chosen scalar threshold quantity; ρ is the Mueller element domain discriminate (also a scalar) given by $\rho=|v|\{\cos[\tan^{-1}(<\underline{M}'_{i,j}>/<\underline{M}_{i,j}>)-\sin[\tan^{-1}(<\underline{M}'_{i,j}>/<\underline{M}_{i,j}>)]\}/2^{1/2}$; v is the Mueller element vector from graphic origin to centroid (one per each grid of FIG. 4), and the magnitude of this vector $|v|=[>\underline{M}_{i,j}>^2+<\underline{M}_{i,j}>^2]^{1/2}$.

FIG. 4. shows a computer graphic display of normalized experimental DIAMMS data as spooled from the lidar sensor's main GUI ('Data Collected' 318 in FIG. 3, right-center window,). Shown are data collected from the original experiment on crystalline enantomers Dextro-rotary D-mannose (red), Levo-rotary L-tartaric acid (blue), and racemic DL-tartaric acid (green) serving as analytic compounds (S) that meet the Mueller domain-component selection rules. The vertical and horizontal axes are $\{M'_{i,j}(\lambda_{on})/M'_{1,1}(\lambda_{on})\}$ and $\{M_{i,j}(\lambda_{off})/M_{1,1}(\lambda_{off})\}$; respectively, where $M'_{i,j}$ and $M_{i,j}$ designate backscattering M-elements on (beam L1) verses off (beam L2) the analyte's absorption band, for all element $i,j\in1,2,3,4\neq1,1$ that are susceptible to the analyte (enantomer surface S). The area bounded by the standard deviation of each data set (intersection of solid horizontal and vertical lines), centered at coordinate $<\{M'_{i,j}(\lambda_{on})/M'_{1,1}(\lambda_{on})\}>$, $<\{M_{i,j}(\lambda_{off})/M_{1,1}(\lambda_{off})\}>$ (dotted cross-hair), designate one detection domain component of the respective analytic compound S—from which that analyte (D-mannose, L-tartaric acid, or DL-tartaric acid) is detected via this DIAMMS method.

As shown in FIG. 5, each display for a Mueller Matrix element data set includes an x-axis component represented by a horizontal dotted line that shows on resonance backscattering (beam L1) and y axis component represented by a vertical dotted line that shows off resonance backscattering (beam L2). The on and off resonance components are bounded by solid lines representing the standard deviation.

CONCLUSION

Embodiments of an OSD 100 according to the present invention may be integrated into a future prototype Chemical-Biological defense photopolarimetric lidar standoff detection system based on differential-absorption Mueller matrix spectroscopy (DIAMMS). The OSD 100 embodies logistics feedback to maintain: (1) switching integrity; (2) a failsafe modus operandi such that beams L1 and L2 are internally confined inside the OSD 100 whenever a systems error is identified during lidar runtime; and (3) synchronization of switching action to vital external functions including operation of two photoelastic modulators to provide photoelastic modulation of beams, retardation adjustment in the PEMs per beam wavelength in [ . . . L1:L2 . . . ], data acquisition (digital or analog) of scattergrams, and graphical presentation of Mueller matrix data element processed from those scattergram waveforms.

Improved use of polarized infrared scattering is achieved in systems that incorporate embodiments according to the present invention. Moreover, such systems may be used to generate a database of susceptible domains via DIAMMS, specific to a class of CB compounds, using significantly less complex in hardware, i.e.; a MMS with fixed-wavelength lasers, stationary POL-PEM:PEM-POL optics, and/or only one (transmitter POL-PEM or receiver PEM-POL) optical pair, software (reduced automation and data handling-processing operations), and firmware (less control, systems checks, and electromechanical and electro-optic manipulations) modalities.

What is claimed is:

1. An optomechanical switching device for a photopolarimetric lidar standoff detection system comprising a plurality of laser beams and a plurality of spectrum analyzers, the optomechanical switching device comprising:

a platform for mounting optical elements;

a translation stage mounted to the platform and selectively translatable along a first axis;

a first mirror mounted on the translation stage and oriented at a predetermined angle to reflect a first laser beam along a second axis substantially orthogonal to the first axis;

a second mirror mounted on the translation stage orthogonally to the first minor and oriented at a predetermined angle to reflect a second laser beam along a second axis;

a third mirror selectively positionable in and out of the path of the second laser beam to deflect the second laser beam to a beam terminator;

a fourth mirror selectively positionable in and out of the path of the first laser beam to deflect the first laser beam to a beam terminator;

a fifth mirror fixed in position and oriented at a predetermined angle to reflect the laser beam from the first mirror to a first spectrum analyzer;

a sixth mirror fixed in position and oriented at a predetermined angle to reflect the laser beam from the second mirror to a second spectrum analyzer;

a seventh mirror selectively positionable in and out of the path of the laser beams thereby deflecting the beams to a beam terminator;

a polarizer in the path of the second axis; and;

a phase shifting element in the path of the second axis.

2. The optomechanical switching device for a photopolarimetric lidar standoff detection system according to claim 1 wherein the phase shifting element comprises a quarter wave plate.

3. The optomechanical switching device for a photopolarimetric lidar standoff detection system according to claim 1 further comprising a beam splitter positioned in the path of the first and second beams to deflect a portion of the first and second beams and a power detector to measure the power from the portion deflected by the beam splitter.

4. The optomechanical switching device for a photopolarimetric lidar standoff detection system according to claim 1, further comprising:

control means to actuate;

a first mode of operation in which the first beam is reflected by the first and fifth mirrors to the first spectrum analyzer and the second beam is reflected by the third mirror to a beam terminator, a second mode of operation in which the first beam is reflected by the fourth mirror to a beam terminator and the second beam is reflected by the second and sixth mirrors to the second spectrum analyzer, a third mode of operation in which the second beam is reflected by the third mirror to a beam terminator and the first beam is reflected by the first mirror through the polarizer and quarter wave plate and out of the optomechanical switching device;

a fourth mode of operation in which the first beam is reflected by the fourth mirror to a beam terminator and the second beam is reflected by the second mirror through the polarizer and quarter wave plate and out of the optomechanical switching device; and a fifth mode of operation in which both the first beam and the second beam are directed to a beam terminator.

5. A switching device for a multiple beam photopolarimetric lidar standoff detection system comprising a plurality of laser beams and a plurality of spectrum analyzers, the switching device comprising:

means for configuring the system into a first mode of operation in which a first laser beam is directed to a first spectrum analyzer and a second laser beam is directed to a beam terminator;

means for configuring the system into a second mode of operation in which the first laser beam is directed to a beam terminator and the second laser beam is to a second spectrum analyzer, means for configuring the system into a third mode of operation in which the second laser beam is directed to a beam terminator and the first laser beam is directed to a backscatter surface;

means for configuring the system into a fourth mode of operation in which the first laser beam is directed to a bean terminator and the second laser beam is directed to a backscatter surface; and means for configuring the system into a fifth mode of operation in which each of the laser beams are directed to a beam terminator.

6. A method of operating a multiple beam photopolarimetric lidar standoff detection system comprising a plurality of laser beams, a plurality of spectrum analyzers and an optomechanical switching device, comprising:

configuring the system into a first mode of operation in which the optomechanical switching device directs a first laser beam to a first spectrum analyzer and directs a second laser beam to abeam terminator;

configuring the system into a second mode of operation in which the optomechanical switching device directs the first laser beam to a beam terminator and directs the second laser beam to a second spectrum analyzer, configuring the system into a third mode of operation in which the optomechanical switching device directs the second laser beam to a beam terminator and directs the first laser beam to a backscatter surface;

configuring the system into a fourth mode of operation in which the optomechanical switching device directs the first laser beam to a beam terminator and directs the second laser beam to a backscatter surface; and configuring the system into a fifth mode of operation in which the optomechanical switching device directs each of the laser beams to a beam terminator.

7. A computer program stored in a computer memory or embodied in computer-readable media comprising program instructions for operating a photopolarimetric lidar standoff detection system comprising an optical switching device, a plurality of laser beams and a plurality of spectrum analyzers, the program instructions including instructions operable to cause at least one programmable processor to:

configure the optical switching device for a first mode of operation in which a first laser beam is directed to a first spectrum analyzer and a second laser beam is directed to a beam terminator;

configure the optical switching device for a second mode of operation in which the first laser beam is directed to a beam terminator and the second laser beam is to a second spectrum analyzer, configure the optical switching device for a third mode of operation in which the second laser beam is directed to a beam terminator and the first laser beam is directed to a backscatter surface;

configure the optical switching device for a fourth mode of operation in which the first laser beam is directed to a beam terminator and the second laser beam is directed to a backscatter surface; and configure the optical switching device for a fifth mode of operation in which each of the laser beams are directed to a beam terminator.

8. The program according to claim 7, further comprising instructions operable to cause at least one programmable processor to provide a graphical user interface which includes icons representing one or more components of the multiple beam photopolarimetric lidar standoff detection system.

9. The program according to claim 7, further comprising instructions operable to cause at least one programmable processor to provide a graphical user interface which includes objects to receive control inputs from an operator.

10. The program according to claim 8, further comprising instructions operable to cause at least one programmable processor to display status information for the one or more components of the multiple beam photopolarimetric lidar standoff detection system.

11. The program according to claim 10 further comprising instructions operable to cause at least one programmable processor to display measurement data provided by the photopolarimetric lidar standoff detection system.

12. The program according to claim 11 wherein the measurement data comprises a 4×4 M array of M-element data sets $\{M'_{i,j}(\lambda_{on})/M'_{1,1}(\lambda_{on})\}$, $\{M_{i,j}(\lambda_{off})/M_{1,1}(\lambda_{off})\}$.

13. The program according to claim 11 wherein measurement data provided by the photopolarimetric lidar standoff detection system is displayed according to predetermined selection rules for ascertaining an analyte's unique identification domain components.

14. The program according to claim 12 wherein the 4×4 M array is displayed as a grid in which each section of the grid comprises ordinate and abscissa coordinates for each of the M-element data sets $\{M'_{i,j}(\lambda_{on})/M'_{1,1}(\lambda_{on})\}$, $\{M_{i,j}(\lambda_{off})/M_{1,1}(\lambda_{off})\}$.

15. The program according to claim 10 further comprising instructions operable to cause at least one programmable processor to display objects that provide operator input options.

16. The program according to claim 12 wherein the display of the M-elements is bounded by a standard deviation on respective data set members $\{M'_{i,j}(\lambda_{on})/M'_{1,1}(\lambda_{on})\}$ and $\{M_{i,j}(\lambda_{off})/M_{1,1}(\lambda^{off})\}$.

17. An optomechanical switching device for a photopolarimetric lidar standoff detection system comprising a plurality of laser beams and a plurality of spectrum analyzers, the optomechanical switching device comprising:

a platform for mounting optical elements;

a translation stage mounted to the platform and selectively translatable along a first axis;

a first mirror mounted on the translation stage and oriented at a predetermined angle to reflect a first laser beam along a second axis substantially orthogonal to the first axis;

a second mirror mounted on the translation stage orthogonally to the first mirror and oriented at a predetermined angle to reflect a second laser beam along a second axis;

a third mirror selectively positionable in and out of the path of the second laser beam to deflect the second laser beam to a beam terminator;

a fourth mirror selectively positionable in and out of the path of the first laser beam to deflect the first laser beam to a beam terminator;

a fifth mirror fixed in position and oriented at a predetermined angle to reflect the laser beam from the first mirror to a first spectrum analyzer;

a sixth mirror fixed in position and oriented at a predetermined angle to reflect the laser beam from the second mirror to a second spectrum analyzer;

a seventh mirror selectively positionable in and out of the path of the laser beams thereby deflecting the beams to a beam terminator;

a polarizer in the path of the second axis;

a phase shifting element in the path of the second axis;

a beam splitter positioned in the path of the first and second beams to deflect a portion of the first and second beams and a power detector to measure the power from the portion deflected by the beam splitter; and control means to actuate:

a first mode of operation in which the first beam is reflected by the first and fifth mirrors to the first spectrum analyzer and the second beam is reflected by the third mirror to a beam terminator, a second mode of operation in which the first beam is reflected by the fourth mirror to a beam terminator and the second beam is reflected by the second and sixth mirrors to the second spectrum analyzer, a third mode of operation in which the second beam is reflected by the third mirror to a beam terminator and the first beam is reflected by the first mirror through the polarizer and quarter wave plate and out of the optomechanical switching device;

a fourth mode of operation in which the first beam is reflected by the fourth mirror to a beam terminator and the second beam is reflected by the second mirror through the polarizer and quarter wave plate and out of the optomechanical switching device; and a fifth mode of operation in which both the first beam and the second beam are directed to a beam terminator.

* * * * *